United States Patent [19]

Nakatsuka et al.

[11] Patent Number: 5,216,147
[45] Date of Patent: Jun. 1, 1993

[54] RADIOACTIVE BENZODIAZEPINE DERIVATIVES

[75] Inventors: Iwao Nakatsuka, Kobe; Masami Okuno, Osaka; Kunio Shiba, Takarazuka; Akira Yoshitake, Kyoto, all of Japan

[73] Assignee: Sumitomo Chemical Company, Limited, Osaka, Japan

[21] Appl. No.: 415,665

[22] Filed: Oct. 2, 1989

Related U.S. Application Data

[62] Division of Ser. No. 253,773, Oct. 5, 1988, Pat. No. 4,885,152.

[30] Foreign Application Priority Data

Oct. 19, 1987 [JP] Japan .................. 62-263543

[51] Int. Cl.⁵ ............. C07D 243/12; A61K 49/02
[52] U.S. Cl. ............................. 540/504; 424/1.1
[58] Field of Search ................. 424/1.1; 540/504

[56] References Cited

U.S. PATENT DOCUMENTS

| | | | |
|---|---|---|---|
| 3,906,003 | 9/1975 | Akatsu et al. | 540/504 X |
| 3,991,048 | 11/1976 | Ishizumi et al. | 540/504 X |
| 4,083,948 | 4/1978 | Davis et al. | 540/504 X |
| 4,280,993 | 7/1981 | Braestrup et al. | 424/11 |
| 4,606,908 | 8/1986 | Bassingthwaighte et al. | 424/11 |

OTHER PUBLICATIONS

Int. J. Appl. Radiat. Isot. 35, 973–976 (1984).
Neuroscience Letters, 48, 115–120 (1984).
J. Psychiatric Res., 19, 609–622 (1985) No. 4.
The Journal of Nuclear Medicine (Abstract Book), vol. 28, No. 4, Apr. 1987 pp. 726–727, Abstract No. 719, New York, NY., US; M. E. VanDort et al.

Primary Examiner—John S. Maples
Attorney, Agent, or Firm—Stevens, Davis, Miller & Mosher

[57] ABSTRACT

The present invention relates to a novel radioactive benzodiazepine derivative represented by the formula:

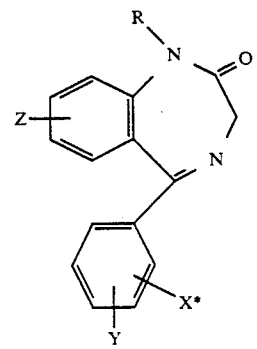

wherein R is hydrogen or a lower alkyl; X* is radioactive iodine or bromine; Y is hydrogen or a halogen; and Z is a halogen or nitro group; and the salt thereof.

The compound of the present invention enables to non-invasively detect the presence of benzodiazepine receptors in human or animal brains, other organs or tissues. Additionally, it enables to dynamically trace the change in receptor concentration either.. It is very useful as a radioactive diagnostic agent for nuclear medicine in vitro or in vivo or as a radiopharmaceutical.

16 Claims, No Drawings

RADIOACTIVE BENZODIAZEPINE DERIVATIVES

This is a DIVISION of application Ser. No. 07/253,773, filed Oct. 5, 1988 now U.S. Pat. No. 4,885,152.

The present invention relates to a novel radioactive benzodiazepine derivative represented by the formula (I):

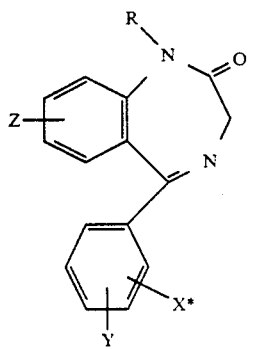

wherein R is hydrogen or a lower alkyl; X* is radioactive iodine or bromine; Y is hydrogen or a halogen and Z is a halogen or nitro group; and the salt thereof (hereafter referred to as the compound of the present invention) as well as processes for producing the same.

The compound represented by the formula (I) is a novel compound not disclosed in any literature and has a very high affinity to benzodiazepine receptors. The compound is very useful as a radioactive diagnostic agent for nuclear medicine in vitro or in vivo or as a radiopharmaceutical. Furthermore, the compound of the present invention is very useful as a radioactive ligand in radioimmunoassay method, as it has a high affinity to benzodiazepine antibodies.

In recent years, it has been found that the amount of benzodiazepine receptors changes in a certain brain disorder (for example, epilepsy, dementia, etc.). In the medical or pharmaceutical field, studies on a relationship between benzodiazepine receptors and various cerebral diseases are of great interest. Under these circumstances, it has been strongly desired to develop diagnostics and radiopharmaceuticals, targetting to benzodiazepine receptors.

As such an approach, compound [C-11]Ro 15-1788 labeled with positron emitter, C-11 has recently been developed and, benzodiazepine receptors in the human brain have been investigated by the PET method [J. Psychiatr. Res., 19, 609 (1985); Radioisotopes, 34, 302 (1985)].

However, the aforesaid method using [C-11]Ro 15-1788 involves many problems in practical use. That is, cyclotron facilities are required in the clinics because C-11 has an extremely short half life. Besides, the labeled compound must be synthesized in a short period of time, etc.

The present inventors have made extensive investigations, aiming at developing benzodiazepine receptor diagnostics and radiopharmaceuticals labeled with radioactive iodine or bromine. As a result, it has been found that the compound represented by the formula (I) defined above has a very high affinity to benzodiazepine receptors and specifically binds thereto. A combination system of a compound selected from the compounds of the present invention with single photon emission computed tomography (SPECT) method solves the aforesaid problems PET method involves. This technique gives not only easy determination or diagnosis of benzodiazepine receptors but also receptor imaging at several hours after administration, which cannot be obtained with [C-11]Ro 15-1788 due to its super short half life. That is, the present inventors have found that the compound of the present invention represented by the formula (I) possesses excellent properties as benzodiazepine receptor targetting diagnostics and radiopharmaceuticals from a practical viewpoint and have accomplished the present invention.

The methods for preparing the compound of the present invention are described below.

The compound of the present invention represented by the formula (I) defined above can be produced according to either Process A or Process B shown below.

Process A

The compound of the present invention represented by the formula (I) defined above can be obtained by an exchange reaction of a benzodiazepine derivative represented by the formula (II):

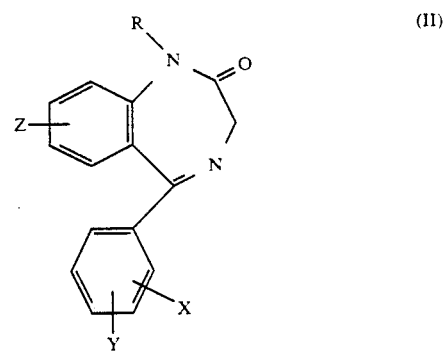

wherein R, Y and Z are the same as defined above and X is iodine or bromine; with a radioactive metal iodide or metal bromide in a solvent, for example, acetonitrile, dimethyl sulfoxide, dimethylformamide, ethylene glycol, an ethereal derivative of ethylene glycol, an ethereal derivative of diethylene glycol, hexamethylphosphorous triamide (HMPT), water or the like, generally at a reaction temperature of 50° to 180° C. followed by a conventional manner such as extraction with a solvent, etc.

Process B

An aminobenzodiazepine derivative represented by the formula (III):

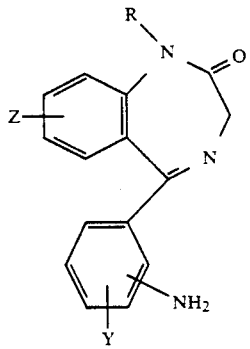

(III)

wherein R, Y and Z are the same as defined above, is allowed to treat with an alkali metal nitrite in a solvent (e.g. tetrahydrofuran, dioxan, acetonitrile) in the presence of an acid (e.g. diluted sulfuric acid, an organic acid) to form a diazonium salt represented by the formula (IV):

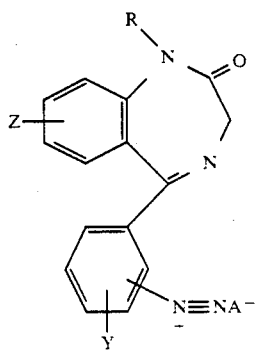

(IV)

wherein R, Y and Z are the same as defined above, $A^-$ is a halogen ion, or an anion having the formula: $HSO_4^-$, the formula:

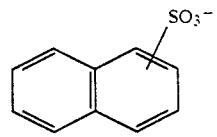

or the formula $R'B^-$ wherein $R'$ is an alkyl, a haloalkyl or an aryl which may be substituted, and B is a substituent having the formula $SO_3$ or $CO_2$.

Then, the diazonium salt represented by the formula (IV) is allowed to treat with a radioactive hydroiodic acid, hydrobromic acid, metal iodide or metal bromide, if necessary, in the presence of copper powders or a copper salt, generally at a temperature ranging from $-5°$ to $30°$ C. Then, the product is isolated in a conventional manner such as extraction with a solvent, etc. to give the compound of the present invention represented by the above formula (I).

The compound of the present invention obtained by either Process A or Process B described above may be purified, if necessary or desired, in a conventional manner such as thin layer chromatography (TLC) or high-performance liquid chromatography (HPLC), etc.

In the present invention, the radioactive iodine includes I-123, I-125, I-131, I-132, etc. with I-123 being preferred. As the radioactive bromine, Br-75, Br-76, Br-77, Br-80, Br-82, etc. are exemplified. The radioactive metal iodide or metal bromide means a metal salt of the above radioactive iodine or bromine, and may be any of those capable of providing a radioactive $I^-$ ion or $Br^-$ ion. Specific examples thereof include sodium iodide, potassium iodide, lithium iodide, sodium bromide, potassium bromide, lithium bromide, etc.

As the halogen atom, fluorine, chlorine, bromine and iodine are exemplified.

The salt of the radioactive benzodiazepine derivative of the present invention refers to a pharmacologically acceptable salt such as salts of the radioactive benzodiazepine derivative with a mineral acid (e.g. hydrochloric acid, sulfuric acid) or those with an organic acid (e.g. acetic acid) etc.

After the radioactive benzodiazepine derivative or salt thereof obtained by the present invention has been intravenously administered to the patient, scintigram is taken with the passage of time or, radioactivity is measured by a probe method or, uptake of the compound into a specific organ or tissue is measured by tomographic images obtained with a SPECT or PET camera, thereby enabling an easy and accurate diagnosis of the regional scope of focus and the degree of disease. Furthermore, the compound of the present invention labeled with, for example, an atom such as I-125 or I-131, can be advantageously used as a radioactive ligand for quantitatively analyzing the benzodiazepine derivative and its metabolite and for estimating the affinity, in radioactive immunoassay using the benzodiazepine antibody, in measurement of the amount of the benzodiazepine derivative in a body fluid sample (e.g. blood, urine, etc.) and in radioreceptor assay using the benzodiazepine receptors.

The following Examples, Reference Examples and Test Examples serve to give specific illustrations of the practice of the present invention but they are not intended any way to limit the scope of the present invention.

The following Reference Examples show the preparation of the compounds used as a raw material for the compounds of the present invention.

REFERENCE EXAMPLE 1

Preparation of
7-chloro-2,3-dihydro-5-(2-iodophenyl)-1-methyl-1H-1,4-benzodiazepine After a mixture of 181 mg of N'-(4-chlorophenyl)-N-(2-iodobenzoyl)-N'-methylethylenediamine, 925 mg of phosphorus pentoxide and 4 ml of phosphorus oxychloride had been stirred at 115° to 120° C. for 4 hours, the reaction mixture was allowed to cool and poured into ice water to decompose an excess of the reagents. After having been washed with ether, the aqueous phase was alkalized with sodium carbonate and then extracted with ethyl acetate. After the organic phase had been washed with water, distilling off the solvent therefrom gave 164 mg of 7-chloro-2,3-dihydro-5-(2-iodophenyl)-1-methyl-1H-1,4-benzodiazepine.

Mass spectrum (70 eV) m/e: 396, 398 (M+)
$^1$H-NMR (CDCl$_3$) δ (ppm): 2.9 (3H, s, CH$_3$), 3.6–3.9 (4H, m, -CH$_2$CH$_2$-), 6.9–7.9 (7H, m, benzene ring H)

REFERENCE EXAMPLE 2

Preparation of
7-chloro-1-methyl-5-(2-iodophenyl)-3H-1,4-benzodiazepin-2-one (2'-iododiazepam)

A THF solution of 158 mg 7-chloro-2,3-dihydro-5-(2-iodophenyl)-1-methyl-1H-1,4-benzodiazepine and a sodium bicarbonate aqueous solution were simultaneously added by drops to a THF solution of N-bromosuccinimide at room temperature. After the mixture had been stirred at the same temperature for additional 30 minutes, water was poured thereinto and the resulting mixture was extracted with ethyl acetate. Purifying the crude product by silica gel column chromatography gave 140 mg of 2'-iododiazepam.

Melting point: 174°–176° C.
Mass spectrum (70 eV) m/e: 410, 412 (M+)
$^1$H-NMR (CDCl$_3$) δ (ppm): 3.4 (3H, s, CH$_3$), 3.8 (1H, d, CH), 4.7 (1H, d, CH), 6.9–7.9 (7H, m, benzene ring H)

REFERENCE EXAMPLE 3

Preparation of
7-chloro-1-methyl-5-(2-bromophenyl)-3H-1,4-benzodiazepin-2-one (2'-bromodiazepam)

In the same procedure as in Reference Example 2, 170 mg of 2'-bromodiazepam were obtained from 200 mg of 7-chloro-2,3-dihydro-5-(2-bromophenyl)-1-methyl-1H-1,4-benzodiazepine obtained according to the Reference Example 1.

Melting point: 145°–146° C.
Mass spectrum (70 eV) m/e: 362, 364 (M+)
$^1$H-NMR (CDCl$_3$) δ (ppm): 3.4 (3H, s, CH$_3$), 3.8 (1H, bd, CH), 4.8 (1H, bd, CH)

REFERENCE EXAMPLE 4

Preparation of
7-nitro-1-methyl-5-(2-iodophenyl)-3H-1,4-benzodiazepin-2-one

A chromic acid solution was added by drops to an acetic acid solution of 158 mg 7-nitro-2,3-dihydro-5-(2-iodophenyl)-1-methyl-3H-1,4-benzodiazepine at room temperature. After having been stirred at the same temperature for additional one hour, the reaction mixture was poured into ice water and alkalized with aqueous ammonia. After the solvent had been distilled off, purifying the resulting crude product by silica gel column chromatography gave 70 mg of 7-nitro-1-methyl-5-(2-iodophenyl)-3H-1,4-benzodiazepin-2-one.

Mass spectrum (70 eV) m/e: 421 (M+)
$^1$H-NMR (CDCl$_3$) δ (ppm): 3.5 (3H, s, CH$_3$), 3.9 (1H, bd, CH), 4.7 (1H, bd, CH), 7.2–8.5 (7H, m, benzene ring H)

REFERENCE EXAMPLE 5

Preparation of
7-chloro-1-methyl-5-(2-fluoro-4-iodophenyl)-3H-1,4-benzodiazepin-2-one (4'-iodofludiazepam)

To a mixture of 165 mg of 4'-aminofludiazepam, 0.8 ml of acetonitrile and a sodium nitrite aqueous solution were added 130 μl of trifluoroacetic acid while cooling the mixture with ice water. The mixture was stirred at the same temperature for 20 minutes. An aqueous solution of potassium iodide was added to the obtained diazonium salt solution followed by stirring at the same temperature for 2 hours. After completion of the reaction, the reaction mixture was extracted with chloroform. The solvent was distilled off to obtain the crude product. Purifying it by silica gel column chromatography gave 160 mg of 4'-iodofludiazepam.

Mass spectrum (70 eV) m/e: 428, 430 (M+)
$^1$H-NMR (CDCl$_3$) δ (ppm): 3.4 (3H, s, CH$_3$), 3.8 (1H, d, CH), 4.8 (1H, d, CH), 7.0–7.7 (6H, m, benzene ring H)

REFERENCE EXAMPLE 6

Preparation of
7-chloro-1-methyl-5-(4-iodophenyl)-3H-1,4-benzodiazepin-2-one (4'-iododiazepam)

In the same procedure as in Reference Example 2, 160 mg of 4'-iododiazepam were obtained from 180 mg of 7-chloro-2,3-dihydro-5-(4-iodophenyl)-1-methyl-1H-1,4-benzodiazepine.

Mass spectrum (70 eV) m/e: 410, 412 (M+)

REFERENCE EXAMPLE 7

Preparation of
7-chloro-1-methyl-5-(3-iodophenyl)-3H-1,4-benzodiazepin-2-one (3'-iododiazepam)

In the same procedure as in Reference Example 2, 140 mg of 3'-iododiazepam were obtained from 182 mg of 7-chloro-2,3-dihydro-5-(3-iodophenyl)-1-methyl-1H-1,4-benzodiazepine.

Mass spectrum (70 eV) m/e: 410, 412 (M+)

The following Examples show the preparation of the compounds of the present invention.

EXAMPLE 1

Preparation of
7-chloro-1-methyl-5-([$^{125}$I]-2-iodophenyl)-3H-1,4-benzodiazepin-2-one ([$^{125}$I]-2'-iododiazepam)

To 10 μl of a DMF solution containing 5 μg of 2'-bromodiazepam were added 1-naphthalenesulfonic acid, copper sulfide and 1 mCi of Na$^{125}$I. After having been heated at 100° C. for 1.5 hours, the reaction mixture was allowed to cool. Purifying the obtained crude product by HPLC (column: Deverosil ® ODS7) gave 0.7 mCi of [$^{125}$I]-2'-iododiazepam. This product was identical with the product obtained in Reference Example 2 in Rf values in TLC and Rt values in HPLC.

EXAMPLE 2

Preparation of
7-chloro-1-methyl-5-([$^{82}$Br]-2-bromophenyl)-3H-1,4-benzodiazepin-2-one ([$^{82}$Br]-2'-bromodiazepam)

To 6 μg of 2'-iododiazepam obtained in Reference Example 2 were added 10 μl of 50% aqueous solution of DMF, 1-naphthalenesulfonic acid, copper sulfide and 2 mCi of Na$^{82}$Br. After having been heated at 100° C. for 2 hours, the reaction mixture was allowed to cool. Purifying the obtained crude product by HPLC gave 1 mCi of [$^{82}$Br]-2'-bromodiazepam. This product was identical with the product obtained in Reference Example 3 in Rf values in TLC and Rt values in HPLC.

EXAMPLE 3

Preparation of
7-nitro-1-methyl-5-([$^{125}$I]-2-iodophenyl)-3H-1,4-benzodiazepin-2-one To 20 μl of DMF solution containing 10 μg of 7-nitro-1-methyl-5-(2-iodophenyl)-3H-1,4-benzodiazepin-2-one obtained in Reference Example 4 were added 1-naphthalenesulfonic acid, copper sulfide and 1 mCi of Na$^{125}$I. After having been heated at 100° C. for 2 hours, the reaction mixture was allowed to cool. Purifying the obtained crude product by HPLC (chloroform-/acetone=9/1) gave 0.6 mCi of 7-nitro-1-methyl-5-([$^{125}$I]-2-iodophenyl)-3H-1,4-benzodiazepin-2-one. This product was identical with the product obtained in Reference Example 4 in Rf values in TLC.

EXAMPLE 4

Preparation of 7-chloro-1-methyl-5-(2-fluoro[$^{125}$I]-4-iodophenyl)-3H-1,4-benzodiazepin-2-one ([$^{125}$I]-4'-iodofludiazepam)

In the same procedure as in Example 3, 0.3 mCi of [$^{125}$I]-4'-iodofludiazepam was obtained from 6 μg of 4'-iodofludiazepam obtained in Reference Example 5. The product was identical with the product obtained in Reference Example 5 in Rf values in TLC.

EXAMPLE 5

Preparation of 7-chloro-1-methyl-5-([$^{125}$I]-3-iodophenyl)-3H-1,4-benzodiazepin-2-one ([$^{125}$I]-3'-iododiazepam)

In the same procedure as in Example 3, 0.3 mCi of [$^{125}$I]-3'-iododiazepam was obtained from 4 μg of 3'-iododiazepam obtained in Reference Example 6. The product was identical with the product obtained in Reference Example 6 in Rf values in TLC.

EXAMPLE 6

Preparation of 7-chloro-1-methyl-5-([$^{125}$I]-4-iodophenyl)-3H-1,4-benzodiazepin-2-one ([$^{125}$I]-4'-iododiazepam)

In the same procedure as in Example 3, 0.5 mCi of [$^{125}$I]-4'-iododiazepam was obtained from 7 μg of 4'-iododiazepam obtained in Reference Example 7. The product was identical with the product obtained in Reference Example 7 in Rf values in TLC.

The following Test Example shows that the compound of the present invention has a very high affinity to benzodiazepine receptors.

TEXT EXAMPLE

2'-Iododiazepam, Diazepam and Fludiazepam were screened as for benzodiazepine binding affinity according to the method reported by Nakatsuka (Life Sciences 36 (2) 113–119, 1985). An aliquot of synaptosomal membrane preparations was incubated at 4° C. for 15 min. with each of the unlabeled competing drugs (2'-Iodoiazepam, Diazepam and Fludiazepam) in different concentration and 3H-diazepam. The incubation was terminated by adding ice-cold Tris-HCl buffer followed by a rapid filtration through a Whatman GF/B filter. The bound 3H-diazepam retained on the filter was extracted with ACS-II (Amersham) and counted. All incubations were conducted in triplicate. Nonspecific binding was determined in tubes containing diazepam. Specific binding was calculated by subtracting the nonspecific binding from the total binding. IC$_{50}$ values, the concentrations of the tested compounds that cause 50% inhibition of the specific 3H-diazepam were determined from the displacement curves obtained. The results were summarized in Table.

TABLE

Inhibitory Potency (Affinity for Benzodiazepine Receptors) of Benzodiazepine Derivatives for 3H-Diazepam to Rat Synaptosomal membranes

| Compound | IC$_{50}$ (M) | Ki (M) | Relative Potency |
|---|---|---|---|
| Diazepam | $9.0 \times 10^{-9}$ | $7.7 \times 10^{-9}$ | 100 |
| Fludiazepam | $1.2 \times 10^{-9}$ | $1.0 \times 10^{-9}$ | 770 |
| 2'-Iododiazepam | $2.5 \times 10^{-10}$ | $2.1 \times 10^{-10}$ | 3600 |

The compound of the present invention enables not only to non-invasively detect the presence of benzodiazepine receptors in human or animal brains, other organs or tissues but also to dynamically trace the change in receptor concentration.

What is claimed is:

1. A radioactive benzodiazepine derivative represented by the formula:

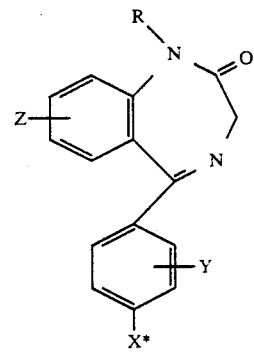

wherein R is hydrogen or lower alkyl; X* is radioactive iodine or bromine; Y is hydrogen or halogen; and Z is a halogen or nitro group located in the 6-, 8- or 9-position; or a salt thereof.

2. A radioactive benzodiazepine derivative or a salt thereof according to claim 1, wherein R is methyl.

3. A radioactive benzodiazepine derivative or a salt thereof according to claim 1, wherein X* is one iodine or bromine isomer selected from the group consisting of I-123, I-125, I-131, I-132, Br-75, Br-76, Br-77, Br-80 and Br-82.

4. A radioactive benzodiazepine derivative or a salt thereof according to claim 3, wherein X* is I-125 or Br-82.

5. A radioactive benzodiazepine derivative or a salt thereof according to claim 3, wherein Z is a bromine, fluorine, iodine or nitro group.

6. A radioactive benzodiazepine derivative or a salt thereof according to claim 5, wherein Z is a nitro group.

7. A radioactive benzodiazepine derivative represented by the formula:

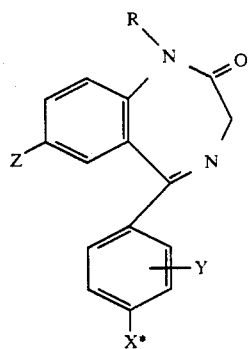

wherein R is hydrogen or lower alkyl; X* is radioactive iodine or bromine; Y is halogen; and Z is a halogen or nitro group; or a salt thereof.

8. A radioactive benzodiazepine derivative or a salt thereof according to claim 7, wherein R is methyl.

9. A radioactive benzodiazepine derivative or a salt thereof according to claim 7, wherein Z is a chlorine or nitro group.

10. A radioactive benzodiazepine derivative or a salt thereof according to claim 7, wherein X* is an iodine or bromine isomer selected from the group consisting of I-123, I-125, I-131, I-132, Br-75, Br-76, Br-77, Br-80 and Br-82.

11. A radioactive benzodiazepine derivative or a salt thereof according to claim 10, wherein X* is I-125 or Br-82.

12. A radioactive benzodiazepine derivative represented by the formula:

wherein R is hydrogen or lower alkyl; X* is radioactive iodine or bromine; and Y is a halogen; or a salt thereof.

13. A radioactive benzodiazepine derivative or a salt thereof according to claim 12, wherein R is methyl.

14. A radioactive benzodiazepine derivative or a salt thereof according to claim 12, wherein X* is an iodine or bromine isomer selected from the group consisting of I-123, I-125, I-131, I-132, Br-75, Br-76, Br-77, Br-80 and Br-82.

15. A radioactive benzodiazepine derivative or a salt thereof according to claim 14, wherein X is I-125 or Br-82.

16. A radioactive benzodiazepine derivative represented by the formula:

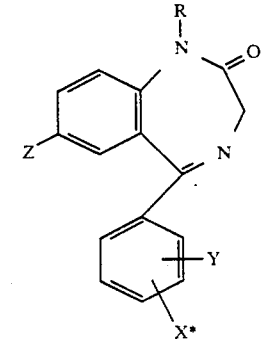

wherien R is hydrogen or a lower alkyl; X* is a radioactive iodine or bromine; Y is hydrogen or a halogen; and Z is a nitro group or a salt thereof.

* * * * *